United States Patent
Freeman et al.

(10) Patent No.: US 9,097,654 B2
(45) Date of Patent: Aug. 4, 2015

(54) ELECTRODE ASSEMBLY

(75) Inventors: Neville John Freeman, Tarporley (GB); Andrew Raymond Mount, Edinburgh (GB); Anthony John Walton, Edinburgh (GB); Jonathan Gordon Terry, Durham (GB)

(73) Assignee: Nanoflex Limited and The University Court Of The University of Edinburgh (GB)

(*) Notice: Subject to any disclaimer, the term of this patent is extended or adjusted under 35 U.S.C. 154(b) by 857 days.

(21) Appl. No.: 13/130,878

(22) PCT Filed: Nov. 30, 2009

(86) PCT No.: PCT/GB2009/051619
§ 371 (c)(1),
(2), (4) Date: Sep. 14, 2011

(87) PCT Pub. No.: WO2011/061229
PCT Pub. Date: Jun. 3, 2010

(65) Prior Publication Data
US 2012/0024571 A1   Feb. 2, 2012

(30) Foreign Application Priority Data
Nov. 28, 2008 (GB) .................................. 0821810.9

(51) Int. Cl.
C25B 11/03  (2006.01)
C25B 11/02  (2006.01)
G01N 27/30  (2006.01)

(52) U.S. Cl.
CPC ............. *G01N 27/307* (2013.01); *C25B 11/02* (2013.01); *B81B 2201/02* (2013.01); *B81B 2203/04* (2013.01)

(58) Field of Classification Search
CPC .... G01N 27/30; G01N 27/3272; C25B 11/00; C25B 11/02; B81B 2203/00; B81B 2204/04; B81B 2201/02
USPC ............... 204/403.03, 280, 290.01, 291, 292, 204/400, 431, 409, 412
See application file for complete search history.

(56) References Cited

U.S. PATENT DOCUMENTS

| 5,670,031 A | * | 9/1997 | Hintsche et al. | ........... 205/777.5 |
| 6,811,663 B1 | * | 11/2004 | Freeman et al. | ............. 204/400 |
| 8,105,469 B2 | * | 1/2012 | Whitehead et al. | ........... 204/409 |

FOREIGN PATENT DOCUMENTS

| WO | WO-9012314 | 10/1990 |
| WO | WO-2007107844 | 9/1997 |

OTHER PUBLICATIONS

International Preliminary Report on Patentability (IPRP) for PCT/GB2009/051916 dated Nov. 30, 2009.

*Primary Examiner* — Luan Van
*Assistant Examiner* — Alexander W Keeling
(74) *Attorney, Agent, or Firm* — Harness, Dickey & Pierce, P.L.C.

(57) ABSTRACT

The present invention relates to an electrode assembly having a laminate structure comprising: a first insulating capping layer; a first conducting layer capped by the first insulating capping layer and substantially sandwiched by at least the first insulating capping layer such as to leave exposed only an electrical contact lip of the first conducting layer; and an array of etched voids extending through at least the first insulating capping layer and the first conducting layer, wherein each void is partly bound by a surface of the first conducting layer which acts as an internal submicron electrode.

23 Claims, 15 Drawing Sheets ns ELECTRODE ASSEMBLY

CROSS-REFERENCE TO RELATED APPLICATIONS

This application is a 371 U.S. National Stage of International Application No. PCT/GB2009/051619, filed Nov. 30, 2009. This application claims priority to British patent application No. 0821810.9 filed with the Intellectual Property Office on Nov. 28, 2008, which is herein incorporated by reference in its entirety.

The present invention relates to an electrode assembly.

The advantages of micro and nano scale electrochemical electrodes have long been recognised. In particular, their small size leads to enhanced mass transport and greater current density due to relatively efficient hemispherical diffusion compared with the planar diffusion characteristic of macroelectrodes. The result is that these systems do not suffer from significant depletion of the electroactive species in the region of the electrode and are therefore not subject to the mass transport effects which typically limit the performance of macroelectrodes. This gives reproducible, quantitative steady-state currents when under mass transport control without the need for forced convection. For example, WO-A-99/60392 discloses a microelectrode system for use in preparative and analytical chemistry having a laminate structure with a number of wells or through holes of micro dimension.

There are a number of disadvantages of micro and nano scale electrodes:

1) They provide very small electrical signals (typically at the pico ampere level) making measurements difficult due to the need to use high performance instrumentation and careful screening of the experimental set up;
2) Due to their small size, these electrodes fabricated using traditional techniques are typically not robust and prone to failure when put under mechanical stress;
3) They tend to be difficult to fabricate using existing methods and particularly difficult to fabricate reproducibly;
4) In many cases hyper-thin layers are not homogeneous and so are prone to breaks in connectivity through "grains" in the structure not being fully in contact with neighbouring grains. This effect can be exacerbated over time by local breaks in connectivity due to external factors such as the mechanical stress often found in thin layers on surfaces of dissimilar structure or surfaces with dissimilar thermal expansion.

Nanoscale electrodes are typically patterned by some form of photolithography that (by definition) requires very high resolution making fabrication very expensive. The limit in terms of electrode size is defined by the resolution of the lithography system. Methods typically used to produce single microelectrodes include the Taylor wire process in which metals such as gold are fed through glass (dielectric) capillaries which are heated and pulled to produce micron scale electrodes encapsulated in glass. Taylor wire electrodes suffer from all of the above deficiencies.

The limitations of micro and nano scale electrodes have proved so significant that in spite of their undoubtedly superior electrochemical performance, they have not made significant commercial impact.

DE-U-29717809 discloses a microelectrode system comprising a laminate structure with at least one conducting layer capable of acting as an internal electrode, at least one dielectric layer of thickness in the range 1 to 1000 microns, an aperture formed in the laminate structure by laser ablation with a diameter of 35 microns and contact means for allowing electrical contact with at least one conducting layer.

EP-A-102042 teaches a macroelectrode system in which individual ion selective electrodes are constructed from disc substrates aligned and bonded together. Each ion selective electrode includes an insulating substrate having a small diameter through hole, a metal layer formed in one body on an inner peripheral surface of the through hole and on major surfaces of the substrate and an ion selective layer formed on the metal layer of the inner peripheral surface.

The present invention seeks to improve the performance of electrodes by the precise and reproducible placement of a conducting layer with controlled dimensions in a laminate structure and the precise and reproducible introduction of internal submicron electrodes into an array of etched voids in the laminate structure.

Thus viewed from one aspect the present invention provides an electrode assembly having a laminate structure comprising:
 a first insulating capping layer;
 a first conducting layer capped by the first insulating capping layer and substantially sandwiched by at least the first insulating capping layer such as to leave exposed only an electrical contact lip of the first conducting layer; and
 an array of etched voids extending through at least the first insulating capping layer and the first conducting layer, wherein each void is partly bound by a surface of the first conducting layer which acts as an internal submicron electrode.

Given the relatively large two-dimensional conducting layer in which each internal submicron electrodes resides, the present invention provides a near infinite number of conduction pathways to each internal submicron electrode. This permits extremely thin conducting layers to be used without a substantial interconnect IR drop between each internal submicron electrode and the external circuitry which is connected to the electrical contact lip (that for example might be experienced by a conventional electrode served by a conducting track). The electrode assembly represents an extremely robust means of addressing multiple internal submicron electrodes of extremely well defined and reproducible geometry which are not readily damaged (unlike a Taylor microwire electrode for example) and have highly efficient and rapid mass transport characteristics.

Other advantageous are
1) With appropriate internal submicron electrode dimensions and void spacing, the internal submicron electrode array may be of macro dimensions but does not suffer from the mass transport limitations of a planar macroelectrode (ie transport to each void is on the micro or nanoscale). The electrode assembly of the invention is capable of passing substantial currents thereby avoiding the requirement for sensitive and expensive test and measurement equipment and/or complex experimental procedures required to monitor low currents;
2) The array is extremely thermally and mechanically robust having high levels of interconnect redundancy in the conduction pathways to each internal submicron electrode even for very thin layers;
3) The array offers robustness in terms of the failure (due to passivation or blockage for example) of an individual internal submicron electrode as all other internal submicron electrodes will continue to function.

Preferably the electrode assembly has at least one or two dimensions on the micrometer to nanometer scale. Preferably the electrode assembly is a microelectrode assembly or a nanoelectrode assembly.

The electrode assembly of the invention may be suitable for use in preparative or analytical chemistry. A material such as an electrolyte may be passed into the etched voids so that only the internal submicron electrodes are exposed to the electrolyte and synthesis, analysis or sequencing may take place.

The layers of the laminate structure may be successively fabricated (eg cast, spun, sputtered, grown or deposited) on each other according to standard techniques.

Preferably the electrode assembly comprises: a plurality of conducting layers (which may be the same or different) including the first conducting layer and a plurality of insulating capping layers including the first insulating capping layer, wherein the plurality of conducting layers and the plurality of insulating capping layers are alternating in the laminate structure, wherein each conducting layer is sandwiched to leave exposed only an electrical contact lip and the array of etched voids extends through the plurality of insulating capping layers and the plurality of conducting layers, wherein each void is partly bound by a surface of each of the plurality of conducting layers which acts as an internal submicron electrode.

The number of internal submicron electrodes in each void may be three, four or five (or more). Such embodiments may be formed by successive lamination (eg deposition or growth) of the conducting layers and insulating capping layers. The dimensions and absolute spatial locations within the void and relative spatial locations of each of the internal submicron electrodes may be precisely defined enabling independent optimisation of the generation and/or detection of multiple electroactive species.

Preferably the electrode assembly further comprises: a second conducting layer, wherein the first conducting layer is sandwiched to leave exposed only a first electrical contact lip and the second conducting layer is sandwiched to leave exposed only a second electrical contact lip, wherein the array of etched voids extends through the first conducting layer, the first insulating capping layer and the second conducting layer, wherein each void is partly bound by a surface of the first conducting layer which acts as an internal submicron electrode and/or by a surface of the second conducting layer which acts as an internal submicron electrode. The first conducting layer and second conducting layer may be substantially coplanar (eg laterally spaced apart). The first conducting layer and second conducting layer may be non-coplanar (eg axially spaced apart, preferably substantially co-axially spaced apart). This may require multilevel metal interconnect.

Preferably the electrode assembly comprises: a second conducting layer and a second insulating capping layer, wherein the first conducting layer is sandwiched to leave exposed only a first electrical contact lip and the second conducting layer is sandwiched to leave exposed only a second electrical contact lip, wherein the array of etched voids extends through the first conducting layer, the first insulating capping layer, the second conducting layer and the second insulating capping layer, wherein each void is partly bound by a surface of the first conducting layer which acts as an internal submicron electrode and/or by a surface of the second conducting layer which acts as an internal submicron electrode. The first conducting layer and second conducting layer may be substantially coplanar (eg laterally spaced apart). The first conducting layer and second conducting layer may be non-coplanar (eg axially spaced apart, preferably substantially co-axially spaced apart). This may require multilevel metal interconnect.

Preferably the array of etched voids is a plurality of discrete sub-arrays of etched voids. The array (or each sub-array) may be a linear or staggered (eg herringbone) pattern. The array (or each sub-array) may be a cubic pattern. The array (or each sub-array) may be a multi-dimensional (eg bi-dimensional) array.

The array of voids may be mechanically or chemically etched according to the desired application. Each void may be an aperture, through-hole, well, tube, capillary, pore, bore or trough. Preferably each etched void is a well. The well may terminate in an insulating capping layer or insulating substrate layer. The well may terminate in a conducting layer which provides an internal submicron electrode in the base of the well.

In accordance with the invention, an array of etched voids of controlled dimension and pitch with an extremely robust interconnect enables higher currents to be measured compared with known individual macroelectrodes. The most advantageous number of etched voids in the array will depend upon the area of the conducting layer, the size of the void, the arrangement of the voids in the array and the desired magnitude of the output signal response.

Preferably the (or each) conducting layer is a substantially planar conducting layer. The (or each) conducting layer may increase in thickness away from the voids. This may serve to reduce IR drop.

Each conducting layer may be made advantageously from a variety of conducting materials thereby enabling specific electrochemistry to be carried out. For example, it may be possible to optimise specific electrochemical generation on a first internal submicron electrode and specific electrochemical product detection on a second internal submicron electrode. In this case, each internal submicron electrode is typically at a different depth in the laminate structure. Simple multi-level connectivity and independent internal submicron electrode control is achievable through the individual exposure in each conducting layer of the electrical contact lip for connection to external circuitry. In this way two or more of the internal submicron electrodes in the array may be effectively connected together.

The (or each) conducting layer may be metallic. The conducting layer may be composed of a noble metal such as gold or silver. Preferred is a metal nitride (eg titanium nitride). The (or each) conducting layer may be an ion exchange polymer. The (or each) conducting layer may be a functionalised (eg chemically or biologically functionalised) metal.

The (or each) insulating capping layer may be polymeric (eg an ion exchange resin). For example, the (or each) insulating capping layer may be composed of poly(ethyleneterephthalate). The (or each) insulating capping layer may be reagent-loaded or functionalised to suit particular applications.

The electrical contact lip may be a peripheral contact edge such as a square contact edge of the conducting layer. The electrical contact lip may be a wide area electrical contact lip (eg the electrical contact lip may extend along substantially the entire length of the periphery of the electrode). The electrical contact lip may be substantially T-shaped. The electrical contact lip allows simple and reliable connection of each internal submicron electrode to external instrumentation eg external circuitry such as a potentiostat for example.

The or each submicron electrode is typically partly or wholly annular.

The (or each) conducting layer may be substantially T-shaped, serpentine or digitated. A serpentine or digitated conducting layer may usefully provide an array of voids with different combinations of internal submicron electrodes on the same level.

In a first preferred embodiment, the first conducting layer is substantially sandwiched by only the first insulating capping layer such as to leave exposed only an electrical contact lip of the first conducting layer, wherein the array of etched voids extends through only the first insulating capping layer and the first conducting layer.

In a second preferred embodiment, the electrode further comprises:
an insulating substrate layer,
wherein the first conducting layer is fabricated on the insulating substrate layer and is substantially sandwiched by the first insulating capping layer and the insulating substrate layer such as to leave exposed only an electrical contact lip of the first conducting layer.

In a third preferred embodiment, the electrode further comprises:
an insulating substrate layer;
a second insulating capping layer fabricated on the insulating substrate layer,
wherein the first conducting layer is fabricated on the second insulating capping layer and is substantially sandwiched by the first insulating capping layer and the second insulating capping layer such as to leave exposed only an electrical contact lip of the first conducting layer.

In a fourth preferred embodiment, the electrode further comprises:
an insulating substrate layer;
a second insulating capping layer,
wherein the first conducting layer is fabricated on the second insulating capping layer and is substantially sandwiched by the first insulating capping layer and the second insulating capping layer such as to leave exposed only an electrical contact lip of the first conducting layer;
a second conducting layer,
wherein the second conducting layer is fabricated on the insulating substrate layer and is substantially sandwiched by the second insulating capping layer and the insulating substrate layer such as to leave exposed only an electrical contact lip of the second conducting layer,
wherein the array of etched voids extends through at least the first insulating capping layer, the first conducting layer and the second insulating capping layer, wherein each void is partly bound by a surface of the first conducting layer which acts as an internal submicron electrode.

Particularly preferably the array of etched voids extends through only the first insulating capping layer, the first conducting layer and the second insulating capping layer.

Particularly preferably the array of etched voids extends through the first insulating capping layer, the first conducting layer, the second insulating capping layer and the second conducting layer, wherein each void is partly bound by a surface of the first conducting layer which acts as a first internal submicron electrode and by a surface of the second conducting layer which acts as a second internal submicron electrode.

In a fifth preferred embodiment, the electrode further comprises:
an insulating substrate layer;
a second conducting layer,
wherein the first conducting layer is digitated and the second conducting layer is digitated, wherein the first conducting layer and the second conducting layer are interdigitally fabricated on the insulating substrate layer and are substantially sandwiched by the first insulating capping layer and the insulating substrate layer such as to leave exposed only an electrical contact lip of the first conducting layer and an electrical contact lip of the second conducting layer,
wherein the array of etched voids extends through the first insulating capping layer, the first conducting layer and the second conducting layer, wherein each void is partly bound by a surface of the first conducting layer which acts as a first internal submicron electrode and is partly bound by a surface of the second conducting layer which acts as a second internal submicron electrode.

In a sixth preferred embodiment, the electrode further comprises:
an insulating substrate layer;
a second conducting layer,
wherein the second conducting layer is substantially coplanar with the first conducting layer, wherein each of the first conducting layer and the second conducting layer is capped by the first insulating capping layer and is substantially sandwiched by at least the first insulating capping layer such as to leave exposed only an electrical contact lip of the first conducting layer and an electrical contact lip of the second conducting layer respectively,
wherein one or more first etched voids extend through the first insulating capping layer and the first conducting layer and one or more second etched voids extend through the first insulating capping layer and the second conducting layer, wherein each first etched void is partly bound by a surface of the first conducting layer which acts as an internal submicron electrode and each second etched void is partly bound by a surface of the second conducting layer which acts as an internal submicron electrode.

Particularly preferably each of the first conducting layer and the second conducting layer is substantially sandwiched by only the first insulating capping layer such as to leave exposed only an electrical contact lip of the first conducting layer and an electrical contact lip of the second conducting layer respectively.

The insulating substrate layer is typically composed of silicon, silicon oxide or a polymeric material.

Optimised hemispherical diffusion of reagents and products in the neighbourhood of each internal submicron electrode will produce optimal signal-to-noise for electrochemical generation and detection. This requires precise control of four independent dimensions in accordance with the present invention. These dimensions (discussed in detail below) include the distance from the bottom of the void (controlled by the etch depth), the distance from the void edge (controlled by the thickness of the layers) and the distance between internal submicron electrodes (controlled by the thickness of the insulating capping layers). These dimensions can be independently and precisely varied for example to maximise the collection efficiency of an internal submicron electrode. This combined with high steady-state currents and signal-to-noise of the internal submicron electrodes makes the assembly of the invention ideally suited for electrochemical generation and detection.

Dimension 1

The thickness ($w_n$) of the $n^{th}$ conducting layer may be determined by fabrication at atomic scale resolution (where atomic scale means a thickness of at least an atom or more). This may be achieved by any conventional deposition or growth fabrication step. This thickness ($w_n$) of the (or each) conducting layer (which may be the same or different) may be in the range of an atomic thickness to 0.99 microns, preferably 0.05 to 0.90 microns, particularly preferably 0.05 to 0.75 microns, more preferably 0.05 to 0.49 microns, most preferably 0.10 to 0.45 microns (eg about 0.23 microns).

Dimension 2

The lateral dimension ($d_w$) and shape of a void determines the distance between opposite faces of the internal submicron electrode. This impacts for example on the time for overlap of the mass transport fields of different parts of the internal submicron electrode and/or the time for metal electrodeposition on the internal submicron electrode to fill the void. For example, if $d_w$ is large compared with the depth of the $n^{th}$ internal submicron electrode ($d_n$), these times are much larger than the time for the diffusion layer to penetrate into the solution from the void.

The cross-sectional shape of the void may be regular. Typically the cross-sectional shape of the void is substantially circular and the lateral dimension is the diameter.

The lateral dimension $d_w$ (eg width or diameter) of each void (which may be the same or different) is typically 0.5 to 1000 microns, preferably 1.0 to 500 microns, more preferably 10 to 100 microns.

When $d_w$ is of micro or nanoscale dimensions, there is enhanced hemispherical diffusion into the void thereby producing a near steady-state response from the entire internal submicron electrode perimeter. This arrangement also has the advantage of in-built interconnection redundancy in the conduction path to the internal submicron electrodes (ie any non-contiguous and hence electrically unconnected areas of the conducting layer will have multiple alternative connecting paths providing in-built redundancy). In the electrode assembly of the present invention, each internal submicron electrode is connected to an electrochemical circuit via multiple parallel pathways through the conducting layer. This means that any local disruption or defects in the conducting layer will not affect the overall connectivity. In other words, all of the internal submicron electrodes are connected via a two dimensional conducting layer to the electrical contact lip.

Dimension 3

The depth of the void is the etch depth ($d_d$). The position of the $n^{th}$ internal submicron electrode at a specified depth ($d_n$) in the void (ie the distance from the aperture opening to the closest edge of the $n^{th}$ electrode) is determined by the width of the insulating capping layer(s). The thickness of the internal submicron electrode ($w_n$) and its position within the void (defined by $d_n$, $d_d$ and $w_n$) can be independently controlled on the micron (or less) scale to produce enhanced transport (increasing with decreasing size) thereby increasing signal-to-noise ratio for electrochemical detection of electroactive species (enhancement 1). The accuracy and reproducibility of the positioning enables reproducible and quantitative diffusion to the internal submicron electrode in the depth direction. The precise minimum distance in this direction from the internal submicron electrode edge to the void edge ($d_n$) can be controlled by controlling the depth of the insulating capping layer(s) to control transport of species into the void.

The thickness of the (or each) insulating capping layer (which may be the same or different) is typically in the range 0.05 to 10 microns, preferably 0.05 to 5 micron, particularly preferably 0.10 to 2.0 microns, more preferably 0.20 to 1.20 microns, most preferably 0.25 to 0.99 microns.

The depth of the first internal submicron electrode (ie the internal submicron electrode closest to the hole edge) ($d_1$) is typically 0.05 to 1000 microns, preferably 0.05 to 100 microns, particularly preferably 0.05 to 10 microns, more preferably 0.10 to 1 micron, most preferably 0.15 to 0.5 microns.

The etch depth of each void (which may be the same or different) ($d_d$) is typically 0.05 to 10000 microns, preferably 0.05 to 1000 microns, particularly preferably 0.05 to 100 microns, more preferably 0.10 to 10 micron.

A judiciously chosen value for $d_n$ combined with the positioning of the internal submicron electrode at the void perimeter will lead to enhanced transport of material into the void thereby increasing signal-to-noise for electrochemical detection of electroactive species from outside the void. This enhancement (enhancement 2) is additional to enhancement 1 and maximum enhancement is achieved by independent optimisation of these two effects.

Dimension 4

The plurality of voids can be arranged in an array with a precisely defined separation or pitch (x and y) using for example standard photolithographic techniques to perform pattern and etch. This permits control for example of the time for overlap of the mass transport depletion zones of different voids.

The pitch (x and y) is typically 0.5 to 10000 microns, preferably 1.0 to 5000 microns, more preferably 10 to 1000 microns.

Preferably x and y are much greater than $d_w$. For example, $x=2d_w$. For example, $y=3d_w$ This minimises interaction through mass transport between voids even at long times and produces near steady-state response from all voids thereby increasing signal to noise for electrochemical detection of the electroactive species in the vicinity of all voids. This will also produce an enhancement of the electrochemical detection of electroactive species outside the void by the internal submicron electrodes in each void (enhancement 3). The overall signal will be governed by the number of voids. For any given array size, there will therefore be an optimum spacing of voids which gives both the largest signal and signal-to-noise. This enhancement (enhancement 3) is additional to enhancements 1 and 2. Maximum enhancement is achieved by independent optimisation of these three enhancements enabling high steady-state currents and therefore excellent signal to noise.

The electrode assembly may further comprise a via to provide an efficient conduction pathway from the face of the internal submicron electrode to the 'back plane' internal submicron electrode which completes the connection to the electrical contact lip.

The present invention lends itself to additional uses that could increase the applicability of experimental measurement (eg by combining electrochemical and optical stimulation and/or measurement). This would be applicable in the case of solutions under test that can be optically stimulated and/or interrogated such as the fluorescent excitation and detection methods used in DNA microarray experiments. In one example, one or more of the insulating capping layers may be an optical waveguide for directing light into and out of the wells. The refractive index of neighbouring layers (conducting layers or insulating capping layers) may be such that efficient internal reflection of the light may occur (as with fibre optics) which may allow for efficient light generation and collection even when these layers were deformed. This would involve the design of an optical interconnect system which may be integrated in to the mask layout of the laminate structure. Many suitable dielectric layers can also be employed as waveguide materials, notably standard fabrication materials such as silicon oxide and silicon nitride. The introduction and collection of the light may take place externally at the periphery of the array and the use of optical interrogation may add sensitivity and/or specificity to a set of experimental results. Wide field illumination and collection may enable the simultaneous stimulation and interrogation of multiple holes, thereby increasing the amplitude of the response. Detection may occur parallel to the incident light (eg for absorption measurements) or perpendicular to the incident light (eg for sensitive luminescence (at a different wavelength to the incident radiation) or scattering (at the same wavelength as the incident radiation) detection). In this approach, optical methods may be used to generate electroactive species, stimulate optical probes or measure optical changes (either in terms of absorbance or in terms of changes in refractive index) or a combination of all of these techniques. These techniques may be made in combination with or separately from electrochemical methods associated with the electrode systems. Optical interrogation may be effected by monitoring the transmitted light or reflected light as is most appropriate. Optical interrogation may also be multiplexed eg by the use of different wavelengths of light through different vertical insulating capping layers for multiple electrode configuration.

In a further aspect, the present invention seeks to address the substantial limitations of the known techniques for fabricating micro and nano scale electrodes without compromising the superior performance of the electrode.

Viewed from a further aspect the present invention provides a process for fabricating an electrode assembly having a laminate structure, said process comprising:
fabricating an insulating capping layer of a predetermined thickness on a conducting layer of a predetermined thickness whereby to leave exposed only an electrical contact lip of the conducting layer,
etching into the conducting layer and insulating capping layer an array of voids each having a predetermined lateral dimension, predetermined depth and predetermined shape.

By predetermining the predetermined parameters of the process of the invention, it is possible to address certain limitations of known processes for preparing microelectrodes.

Preferably prior to step (a) or (b), the process further comprises: fabricating the conducting layer on an insulating substrate layer.

The present invention will now be described in a non-limitative sense with reference to Examples and the accompanying Figures in which FIG. 1a illustrates in side view, side elevation and plan view a first embodiment of the present invention with single internal submicron electrodes;

Figure 7:
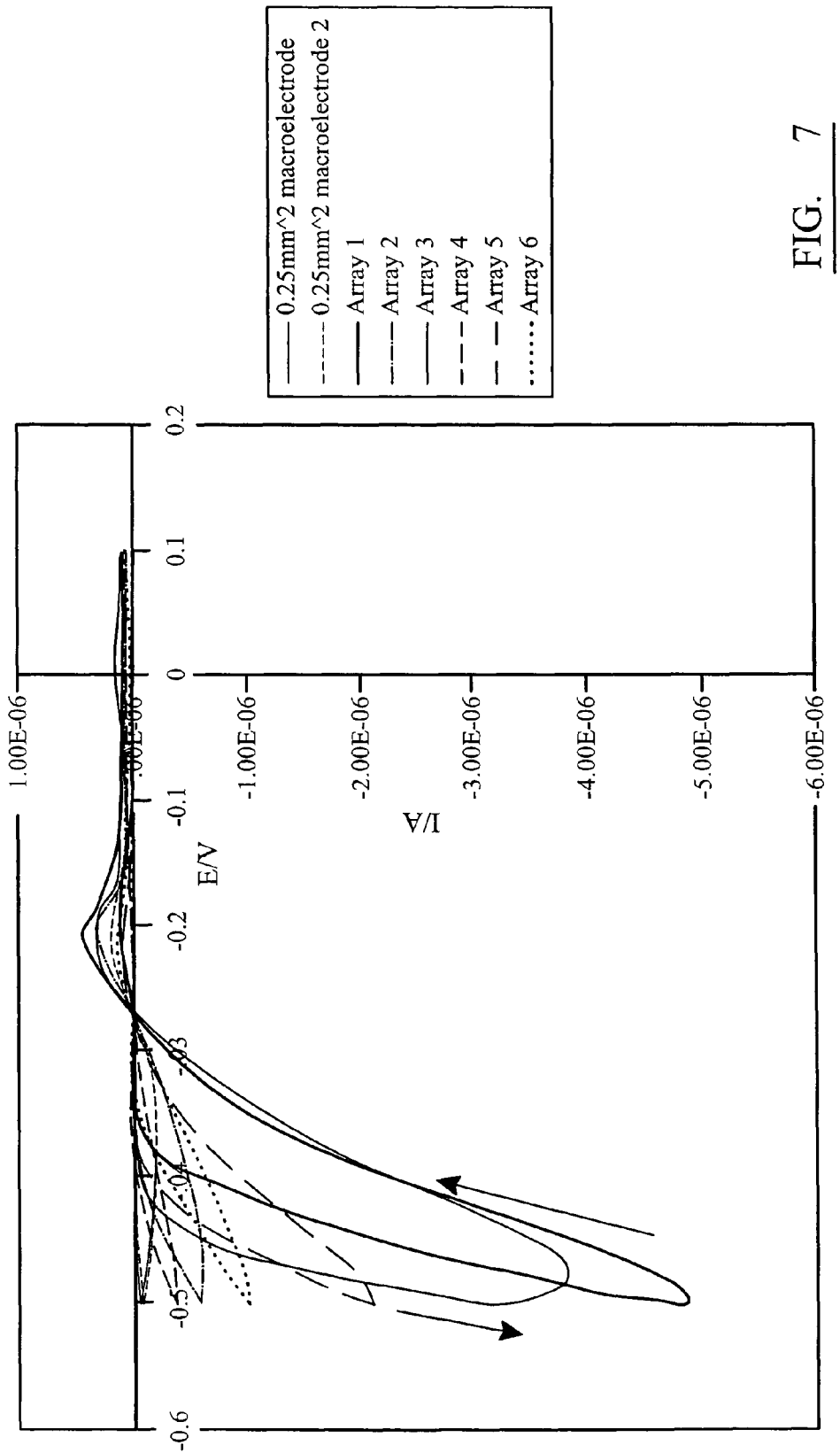
Figure 8:
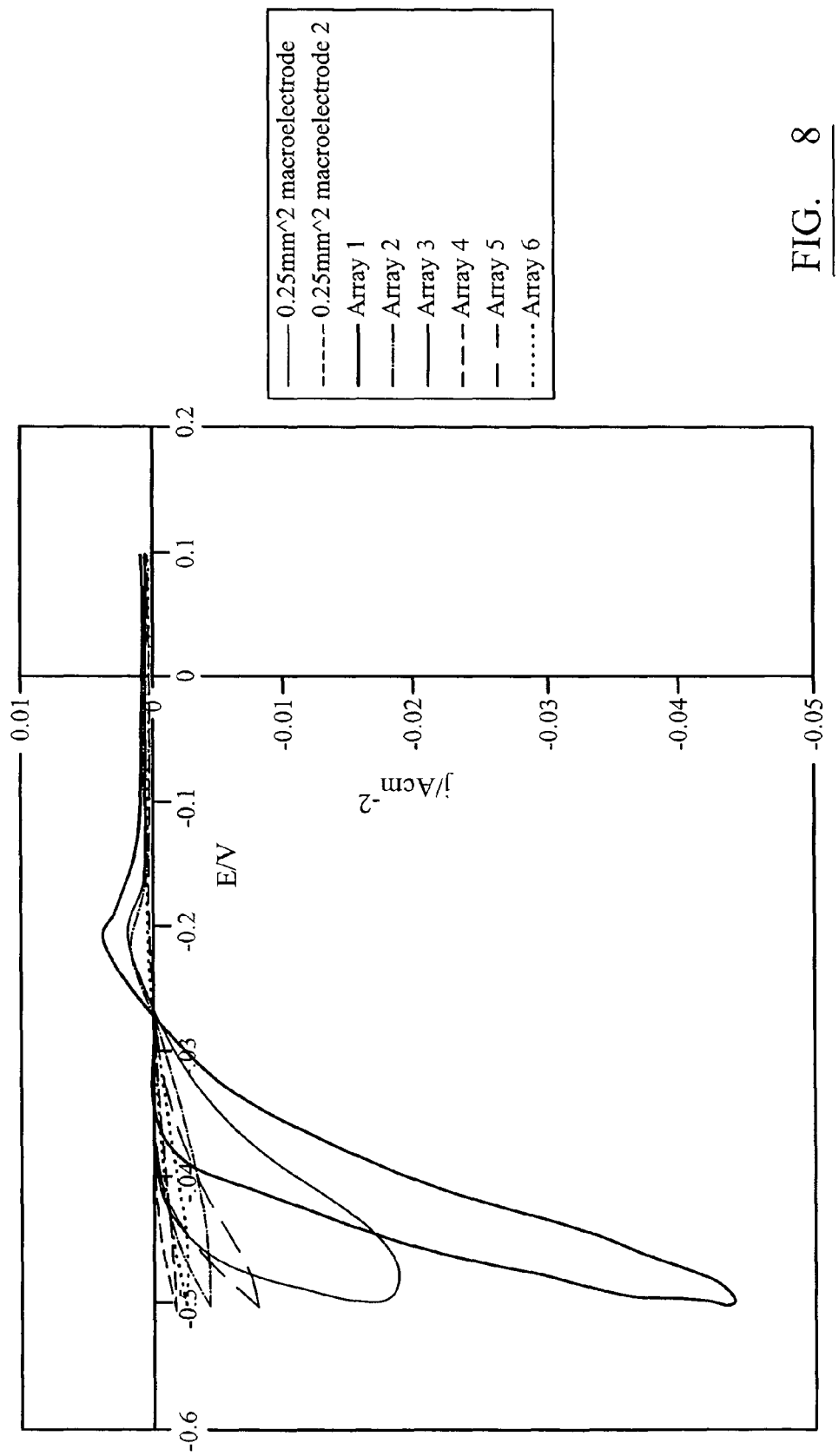
Figure 9:
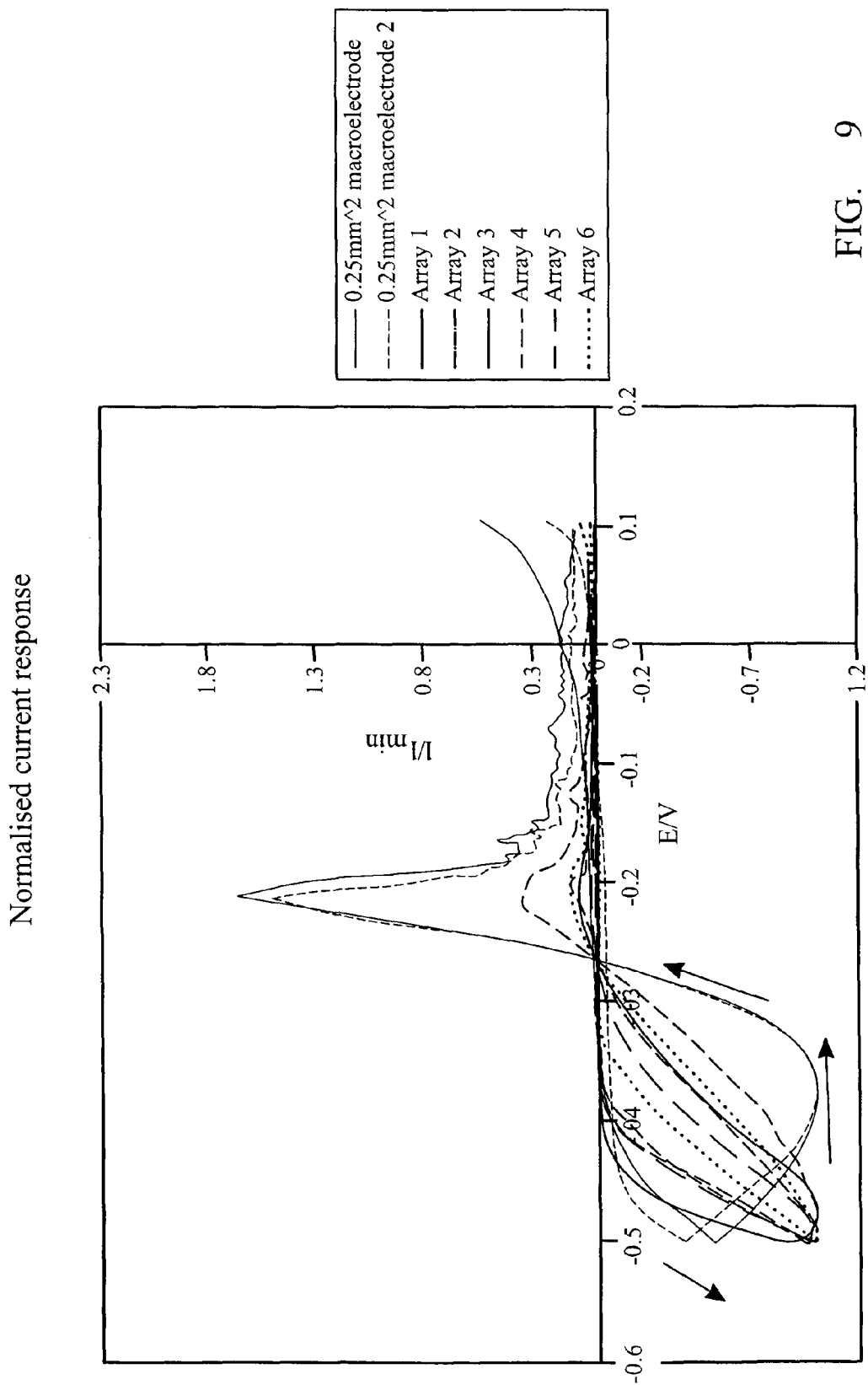
Figure 10:
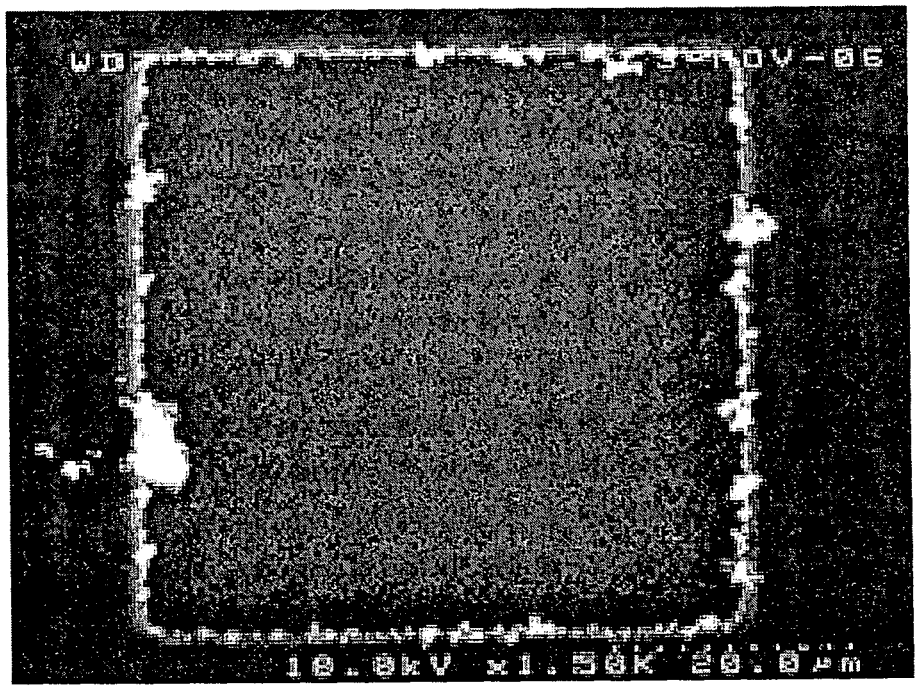
Figure 11:
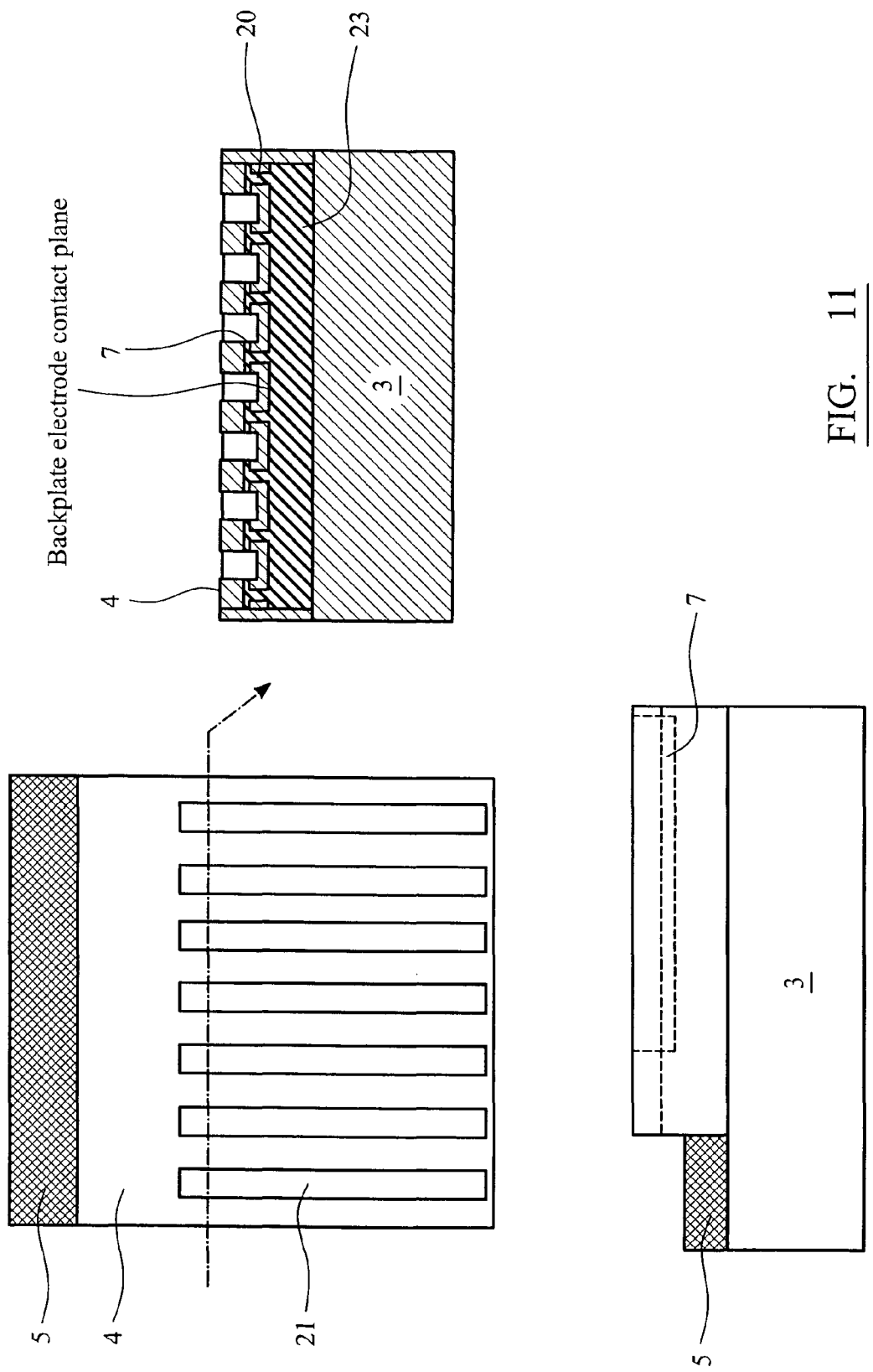
Figure 12:
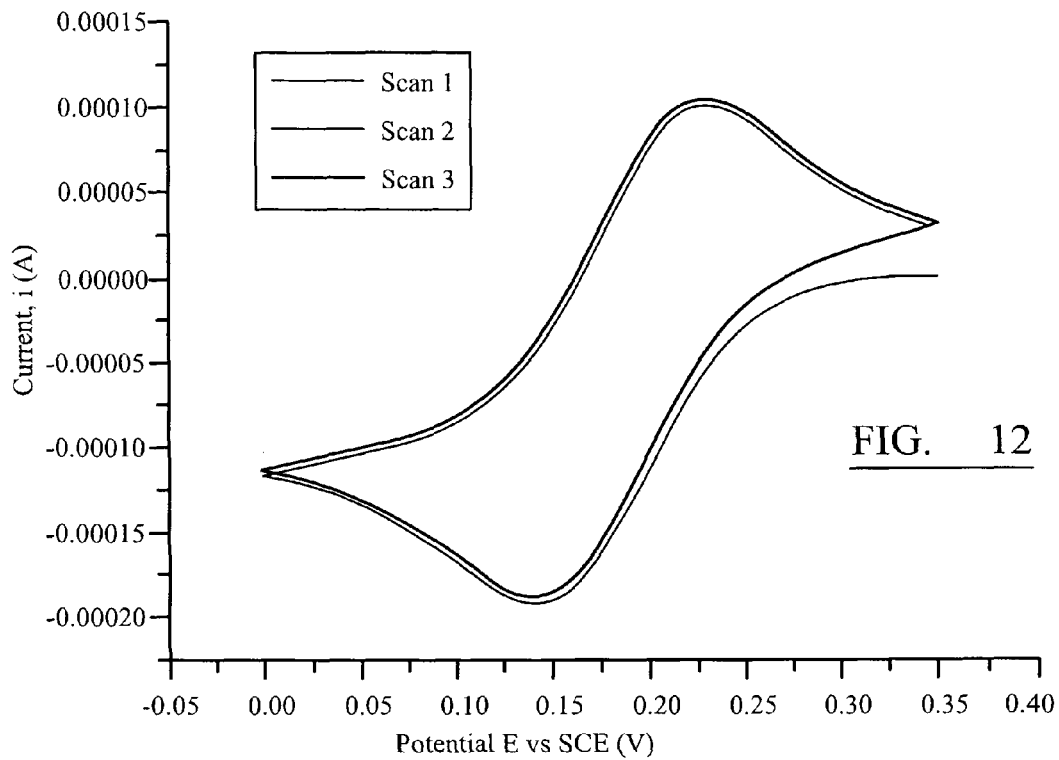
Figure 13:
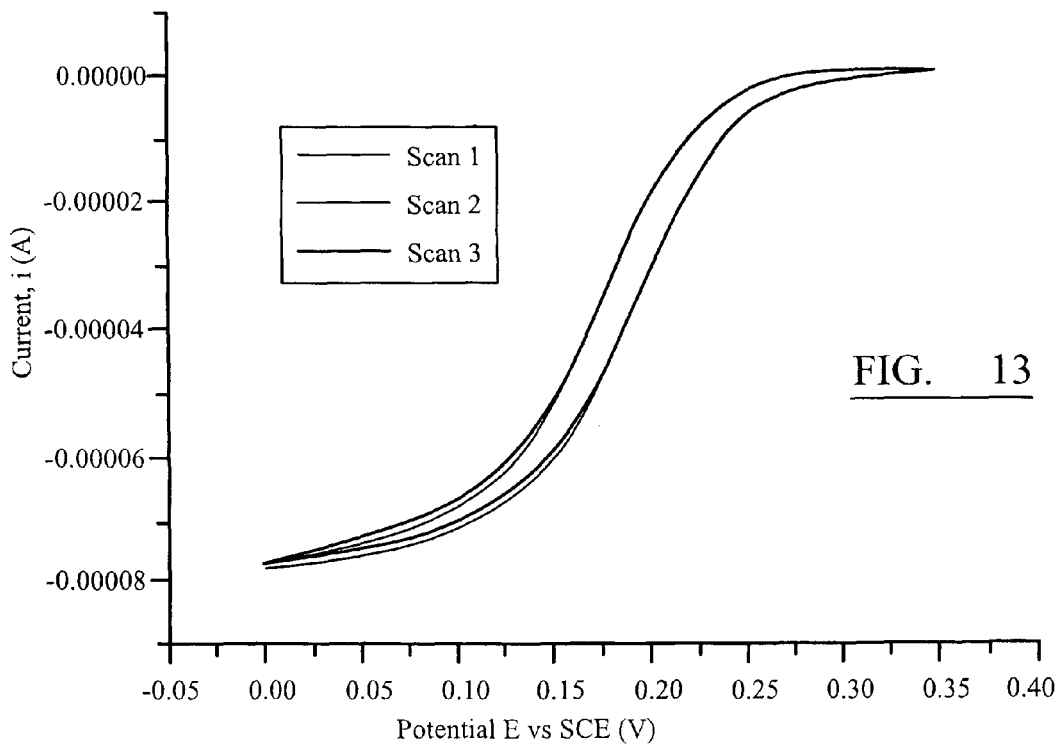
Figure 14:
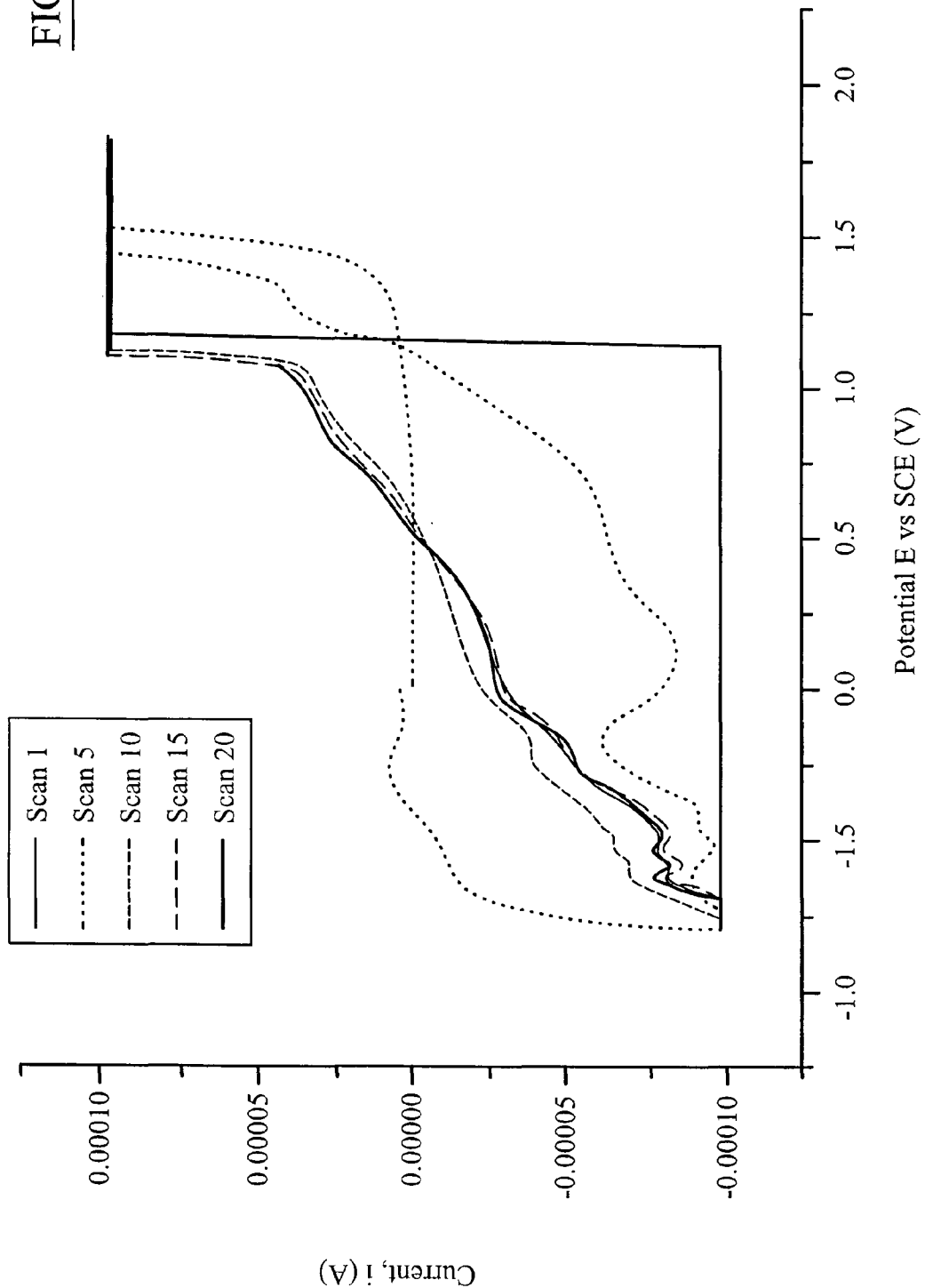

FIG. 7—Cyclic voltammograms (CVs) for the deposition and stripping of silver on TiN array square microhole internal submicron electrodes (from 10 mM AgNO$_3$ in 2 M KSCN, 10 mV s$^{-1}$) using different internal submicron electrode array sizes in comparison to two conventional 0.25 mm$^2$ square TiN macrointernal submicron electrodes. The separation between holes was $d_w$ in the x-direction and $2d_w$ in the y-direction. The arrows show the direction of CV sweep;

FIG. 8—CV data from FIG. 7 with current replaced by the current density (j) calculated from the total internal submicron electrode area;

FIG. 9—CV data from FIG. 7 with the current (I) normalised to the peak reduction current ($I_{min}$);

FIG. 10—Typical SEM picture of a 50 μm microhole internal submicron electrode (top view) after Zn plating using a constant potential of −1.10 V with the established plating protocol;

FIG. 11 illustrates in side view, side elevation and plan view a ninth embodiment of the present invention with vias;

FIG. 12 illustrates a typical diffusion limited response under non-hydrodynamic (unstirred) conditions;

FIG. 13 is a sigmoidal cyclic voltammogram showing three scans of a platinum 0.05 micron thick CAVIAR electrode; and FIG. 14 is a cyclic voltammogram for a 0.05 micron thick platinum CAVIARE electrode between 1.8 and −0.8 V at a sweep rate of 100 mVs$^{-1}$ with the overall current limited to 10 μA.

Figure 1A:
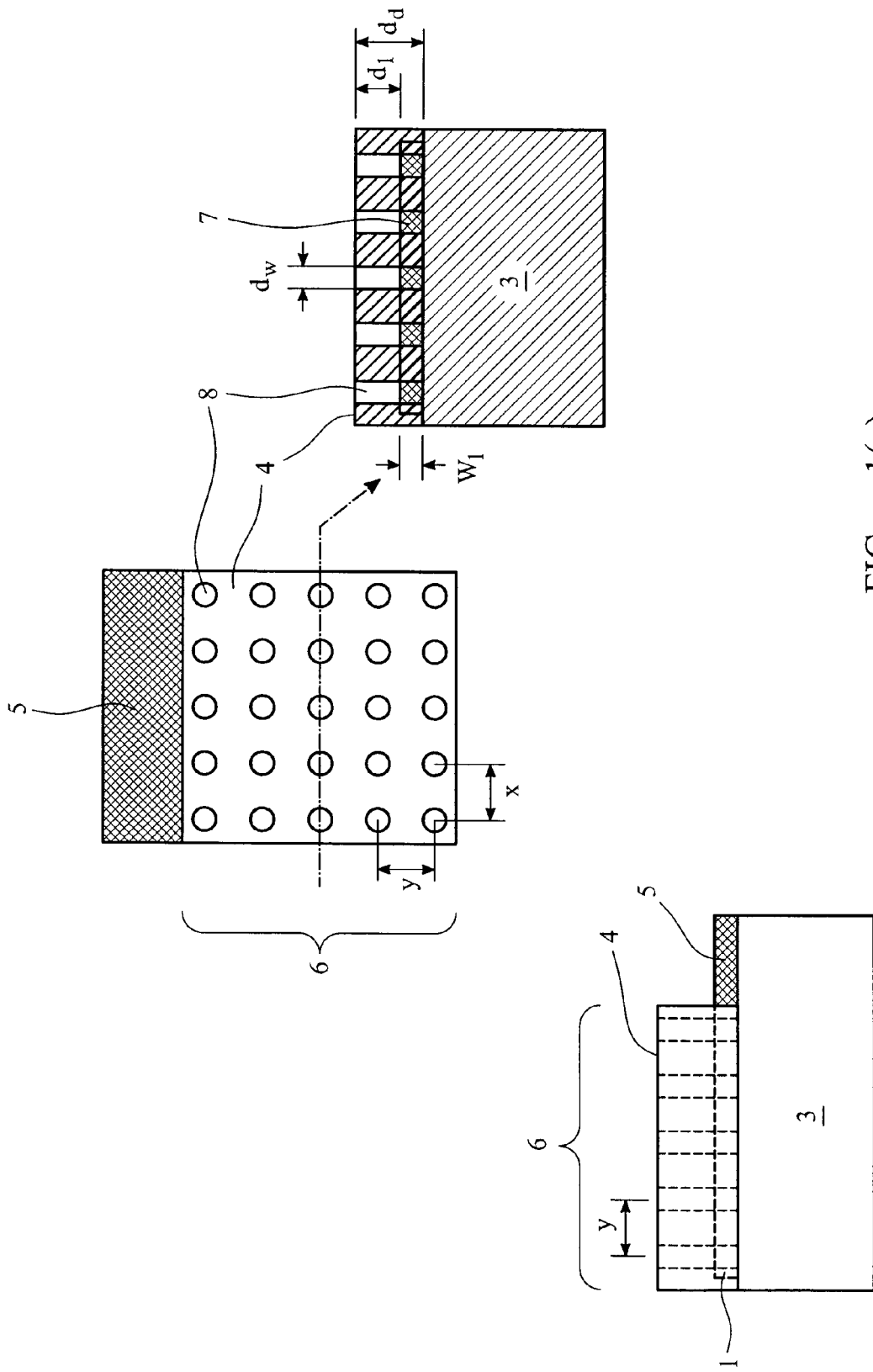
FIG. 1b illustrates in side view, side elevation and plan view a second embodiment of the present invention with single internal submicron electrodes.

FIG. 1(a) illustrates a first embodiment of the laminated internal submicron electrode assembly of the invention comprising a conducting layer 1 on an insulating substrate layer 3. An insulating capping layer 4 covers the conducting layer 1 leaving exposed only an electrical edge contact 5. An array 6 of wells 8 are etched into the insulating capping layer 4 and the conducting layer 1. A single internal submicron electrode 7 is defined in each well 8.

EXAMPLE 1

Figure 1B:
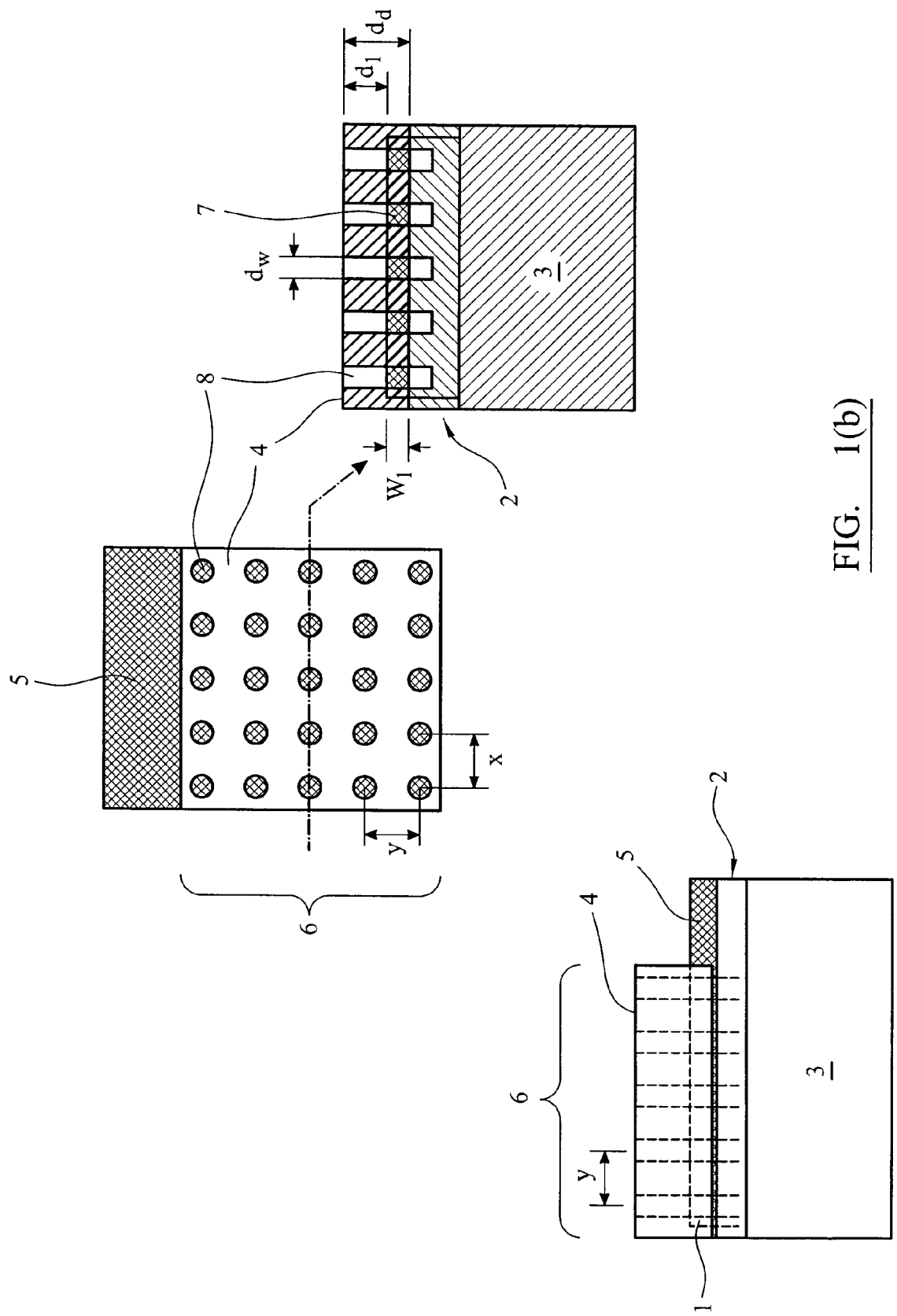

FIG. 1(b) illustrates a second embodiment of the laminated internal submicron electrode assembly of the present invention with single internal submicron electrodes fabricated as follows. A conducting layer 1 of titanium nitride (thickness $w_1$=0.23 microns) was deposited on an insulating capping layer 2 of silicon oxide (thickness=0.5 microns) which had been thermally grown on a silicon wafer substrate 3. An insulating capping layer 4 composed of Parylene® (thickness=1.0 microns) was deposited over the extent of the conducting layer 1 with the exception of one edge which was left exposed to act as an electrical edge contact 5 for direct and simple connection to a potentiostat.

After the layers 1 and 4 had been deposited, a photoresist film was spun onto the insulating capping layer 4. A mask with a number of arrays of holes with a range of six hole sizes (square as opposed to circular as shown in FIG. 1(b) with the hole edge size $d_w$ from 10 to 100 microns) was used to define a number of arrays 6 of wells 8 of different sizes and spacings each containing a single internal submicron electrode 7 as follows:
(1) 119 holes (17×7) @ $d_w$=100 μm;
(2) 198 holes (22×9) @ $d_w$=75 μm;
(3) 442 holes (34×13) @ $d_w$=50 μm;
(4) 840 holes (56×14) @ $d_w$=30 μm;
(5) 1445 holes (85×17) @ $d_w$=20 μm;
(6) 4250 holes (170×25) @ $d_w$=10 μm.

The pitch between hole centres was $2d_w$ in the x-direction and $3d_w$ in the y-direction such that the holes occupied ⅙ of the total area of the array 6. The wells 8 were etched through the Parylene® insulating capping layer 4 using an oxygen plasma and the conducting layer 1 and to a shallow depth the silicon oxide insulating substrate layer 3 were etched using a chlorine based, reactive ion etch. In the final fabrication step, the photoresist layer was removed.

The fabrication process allowed single internal submicron electrodes 7 in different arrays 6 of wells 8 to be tested on a single insulating substrate layer 3. The arrays 6 which were not to be tested were passivated by the application of an acetone soluble polymer. This was simply reversed when required by the application of acetone. The internal submicron electrodes 7 were connected in a straightforward manner to conventional electrochemical equipment.

Cyclic voltammograms for the deposition and stripping of silver from arrays 1 to 6 are shown in FIG. 7 in comparison to two conventional 0.25 mm² square macroelectrodes. It can be seen immediately that the currents obtained for arrays 1 to 6 are larger than for the macroelectrodes. This demonstrates that the electrode assembly of the invention produces currents comparable to (indeed greater than) macroelectrodes. This is in spite of the fact that the total electrode areas (0.011, 0.014, 0.021, 0.023, 0.027 and 0.039 mm² for arrays 1 to 6 respectively) are much smaller than the macroelectrode area. This is further demonstrated by plotting the current density for each electrode system obtained by dividing the current by the total electrode area (see FIG. 8). The current densities obtained with the microelectrode arrays are much larger (of the order of 500 times for array 1) than those obtained with the macroelectrodes whose response is not significant on this current density scale. Since the magnitude of the electrode noise (eg due to electrode double layer charging) is typically governed by electrode area, this increase in current density typically should lead to a corresponding increase in signal-to-noise and hence an increase in detection sensitivity. Such increases are characteristic of micro/nano electrode systems (with their enhanced hemispherical mass transport) but as FIG. 7 shows for these arrays, this also results in a total current which is greater than for the macroelectrodes.

FIG. 9 shows the voltammograms normalised to the peak reduction current. It is clear that all the electrodes show nucleation with the initial reduction in current due to the onset of Ag deposition near −0.37 V vs SCE (characteristic of Ag deposition on TiN (see H. Cesiulis and M. Ziomek-Moroz, Electrocrystallisation and internal submicron electrodeposition of silver on titanium nitride, *J. Appl. Electrochem.*, 30, 1261-1268 (2000))) and deposition in the reverse scan typically occurring at potentials at or below −0.27 V (characteristic at this concentration of electroreduction of Ag⁺ and deposition of Ag onto an Ag surface). The macroelectrodes each show large nucleation loops consistent with very slow Ag nucleation and growth and relatively large oxidative stripping peaks indicating that much of the deposited Ag is able to be oxidatively stripped as Ag⁺. In contrast, the electrode assembly of the invention shows much smaller nucleation loops and near steady-state currents consistent with enhanced Ag nucleation and deposition rates. This is consistent with the deposition of bulk Ag. The relatively small oxidation peaks seen for Ag stripping with these arrays suggests this bulk Ag is more stable to Ag oxidation and stripping.

A similar response was found when electrodepositing Zn from $Zn^{2+}$ solution (according to the protocol outlined in E. Ferapontova, J. G. Terry, A. J. Walton, C. P. Mountford, J. Crain, A. H. Buck, P. Dickinson, C. J. Campbell, J. S. Beattie, P. Ghazal, A. R. Mount, *Electrochem. Comms.*, 9 303-9 (2007)) with a constant deposition potential of −1.10V. Scanning Electron Microscopy (SEM) pictures of the deposited metal (FIG. 10) show deposition at essentially the entire perimeter of the void consistent with efficient internal submicron electrodeposition. As $d_w$ is very large compared to the size of the deposited Zn, prolonged growth of bulk Zn is clearly possible with this configuration, The following demonstrates the exceptional enhancements that this invention brings to an electrode assembly. Taking the example of a 25 micron square hole with electrode structure described above, the electrode area is $2.3 \times 10^{-5}$ mm² and the performance of an array of wells can be compared with a 0.25 mm² conventional electrode. To provide the same electrode area, 10869 holes would need to be defined. However, given that these electrodes are 500 times more efficient, only 22 such voids would be required to provide the equivalent current. If it is assumed that the voids can be equally spaced with an additional 25 micron spacing between voids in both the x and y directions, an array of 5×5 holes would provide a superior signal-to-noise performance when compared with a conventional planar electrode requiring a footprint of 0.25× 0.25 mm (ie one quarter the area of the planar electrode). Thus not only does the approach achieve a high signal-to-noise with exceptional mass transport characteristics in a simply constructed manner but it also allows for smaller electrochemical devices to be constructed (ie nano or micro electrode arrays) which pass equivalent currents to conventional macroelectrodes.

The void may be a slot or trench in a further embodiment. For example, a 10 micron wide trench which is 0.5 mm long which is repeated every 10 microns provides a total of 25 repeats (ie occupies a 0.5 mm² footprint). As a consequence of the electrochemical efficiencies, this electrode would not only have all the advantages of a microelectrode but would also have an order of magnitude greater signal-to-noise than its conventional counterpart. Any design of slot, trench, serpentine, etc. can be used to achieve the desired electrochemical performance and footprint.

In conclusion, this demonstrates that this approach can be used with extremely thin conducting layers (in this case 0.23 µm) without experiencing significant IR drop or wetting problems whilst using conventional equipment and obtaining excellent signal to noise in the response.

EXAMPLE 2

Figure 2:
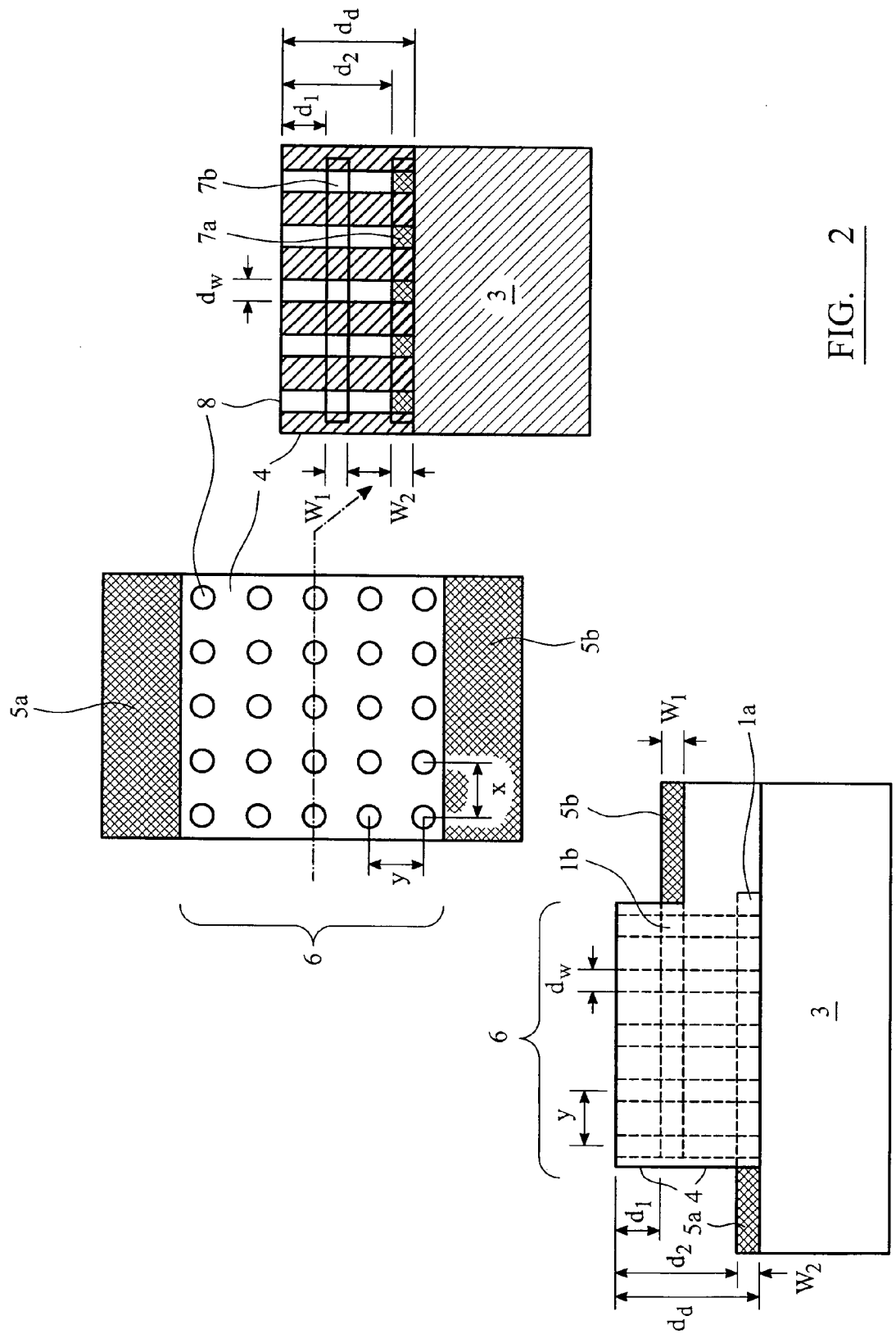
FIG. 2 illustrates in side view, side elevation and plan view a third embodiment of the present invention with dual internal submicron electrodes.

FIG. 2 illustrates a third embodiment of the electrode assembly of the invention with dual internal submicron electrodes. The assembly comprises an array 6 of wells 8 each containing dual internal submicron electrodes 7a and 7b formed at different depths in conducting layers 1a and 1b respectively. The internal submicron electrodes 7a and 7b are addressed through opposite electrical edge connectors 5a and 5b. These could if necessary be arranged on the same edge or in the manner most appropriate to the given application. The size of each well is controlled by $d_w$. The spacing of the wells 8 is controlled by x and y. The geometric (or otherwise) spacing of the internal submicron electrodes 7a, 7b and the collection and/or generation of electrochemical species and their kinetics is controlled by $d_1$, $d_2$, and $d_d$ (in addition to $d_w$) as discussed above. The size of internal submicron electrode 7b is controlled by $w_1$ and $d_w$ and the size of internal submicron electrode 7a is controlled by $w_2$ and $d_w$.

EXAMPLE 3

Figure 3:
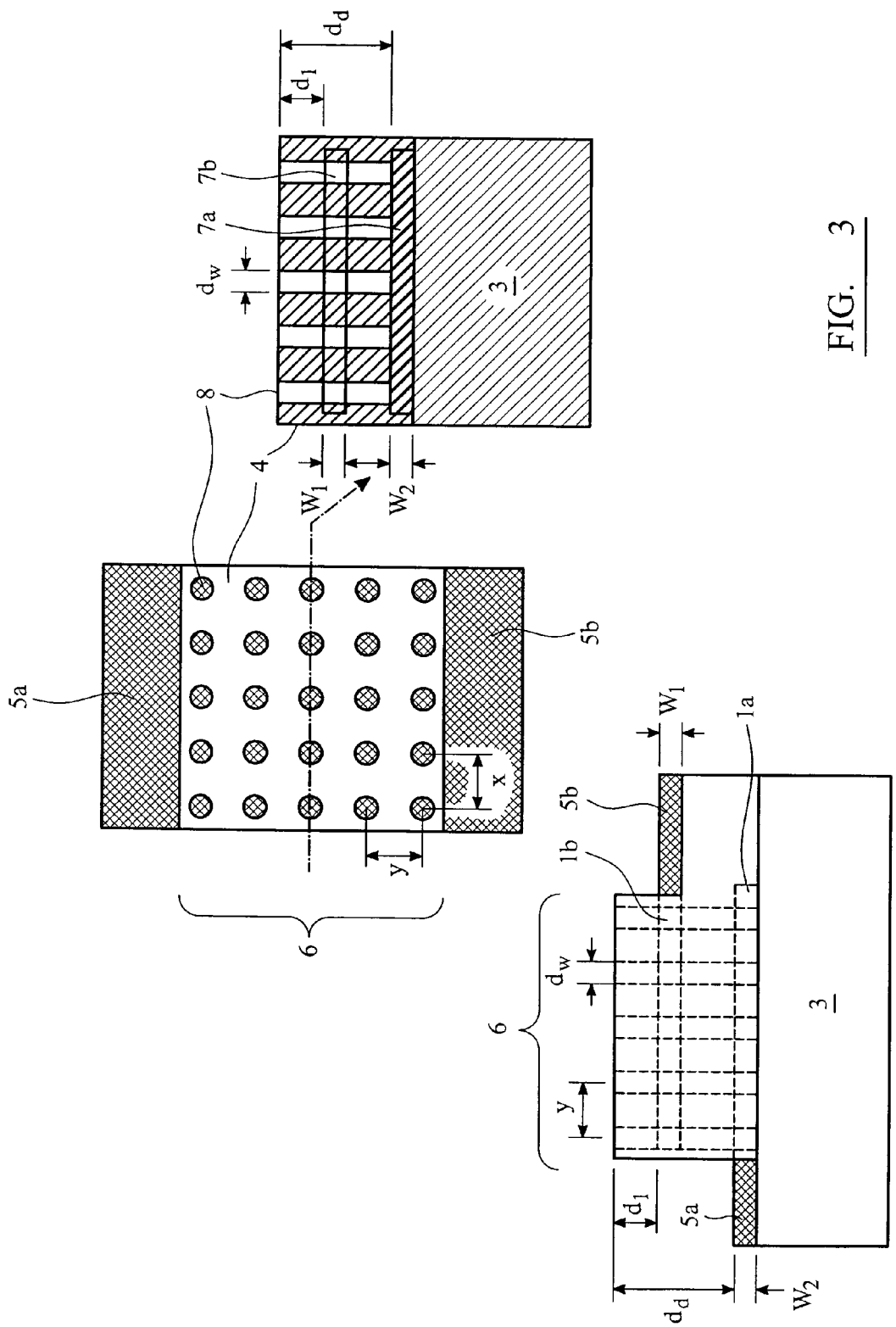
FIG. 3 illustrates in side view, side elevation and plan view a fourth embodiment of the present invention with a terminal internal submicron electrode.

FIG. 3 illustrates a fourth embodiment of the electrode assembly of the present invention with a terminal internal submicron electrode. The assembly comprises an array 6 of wells 8 each containing an internal submicron electrode 7b formed in a conducting layer 1b. Conducting layer 1a is non-etched and forms a terminal internal submicron electrode 7a in each well 8. The internal submicron electrodes 7a and 7b are addressed through opposite electrical edge connectors 5a and 5b. The terminal internal submicron electrode 7a may be exploited as a counter and or reference internal submicron electrode.

Three (or more) internal submicron electrode systems are a simple extension of the above arrangement except that extra lithography and etch steps are required to expose the contacts required to electrically access each internal submicron electrode.

EXAMPLE 4

Figure 4:
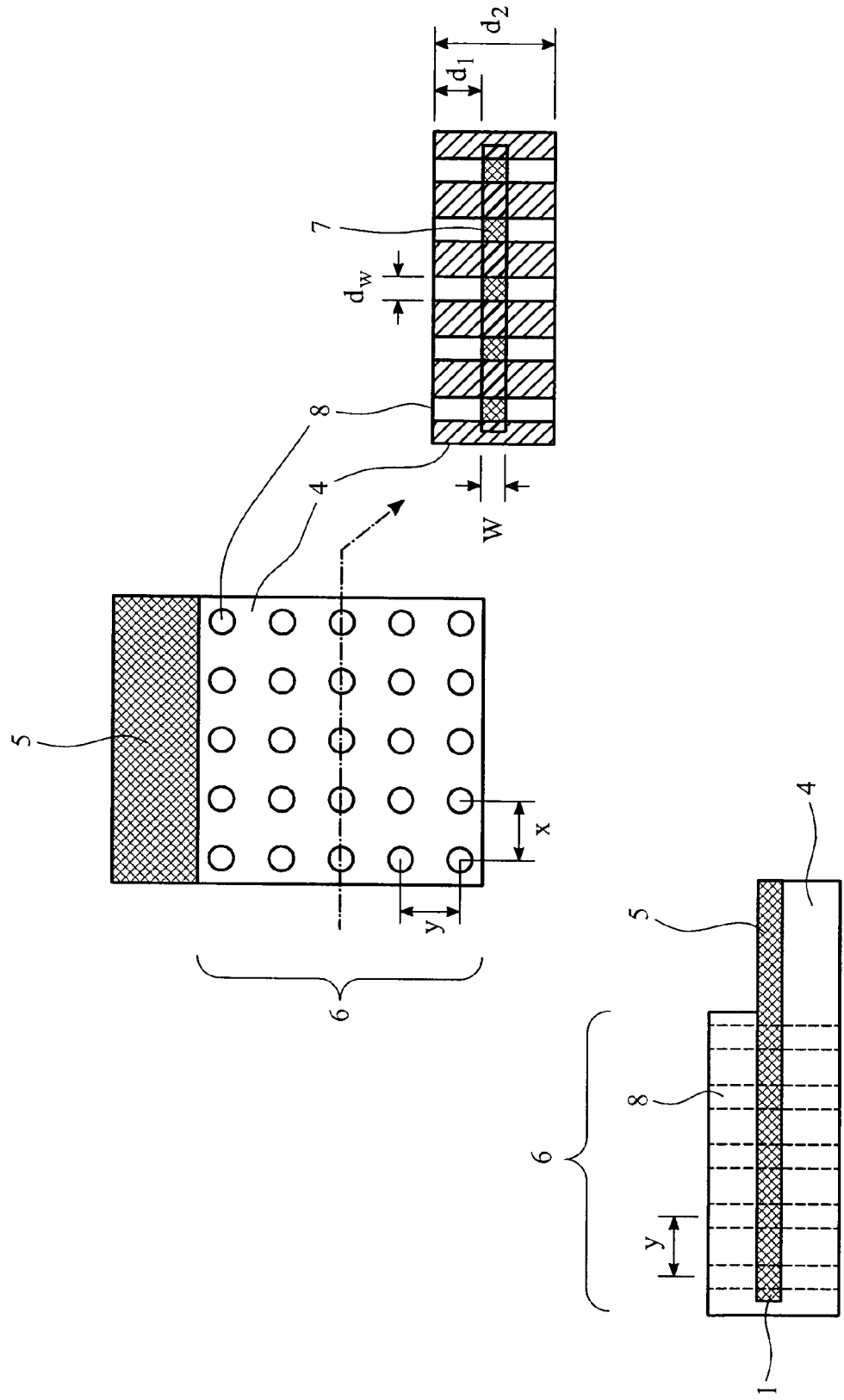
FIG. 4 illustrates in side view, side elevation and plan view a fifth embodiment of the present invention with single internal submicron electrodes and no substrate layer.

FIG. 4 illustrates a fifth embodiment of the internal submicron electrode assembly of the present invention with no substrate. The assembly comprises an array 6 of wells 8 each containing an internal submicron electrode 7 formed in a conducting layer 1. The internal submicron electrode 7 is addressed through an electrical edge connector 5.

EXAMPLE 5

Figure 5A:
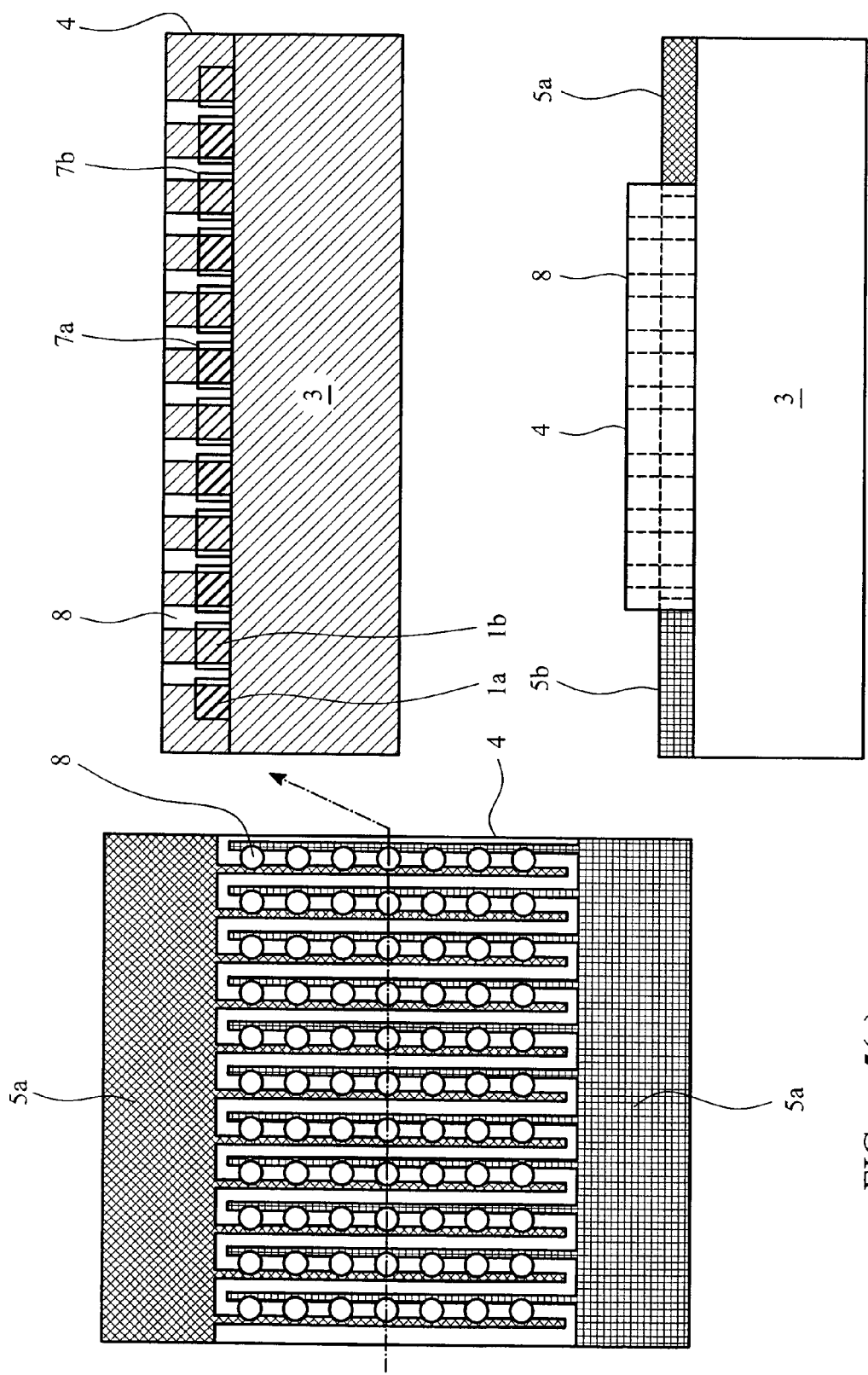
FIG. 5a illustrates in side view, side elevation and plan view a sixth embodiment of the present invention with interdigitated internal submicron electrodes.
Figure 5B:
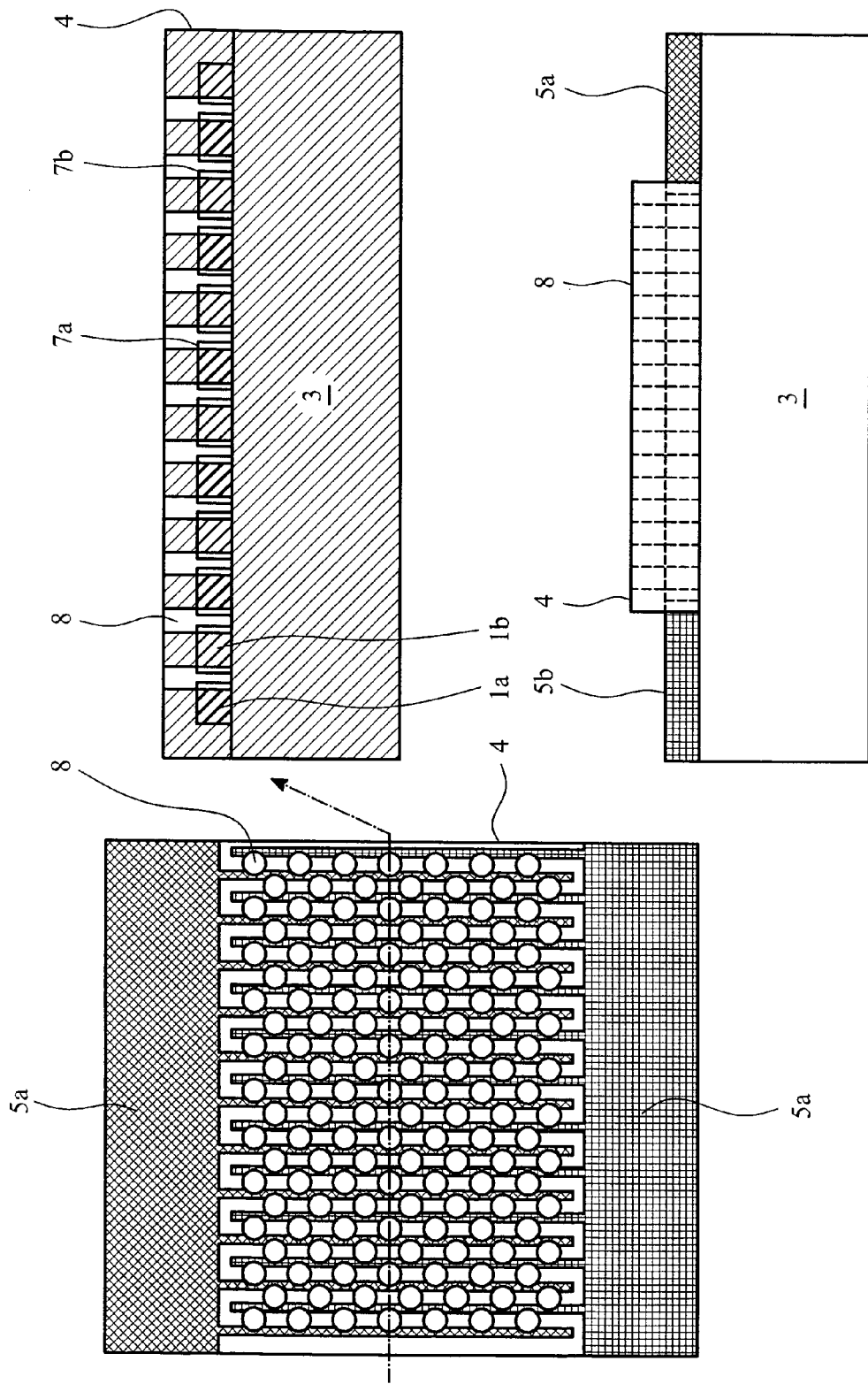
FIG. 5b illustrates in side view, side elevation and plan view a seventh embodiment of the present invention with interdigitated internal submicron electrodes.

FIG. 5(*a*) illustrates a sixth embodiment of the electrode assembly of the present invention with interdigitated conducting layers. A digitated conducting layer 1a and a digitated conducting layer 1b are interdigitated on an insulating substrate layer 3. The assembly comprises an array 6 of wells 8 each containing an internal submicron electrode 7b formed in the digitated conducting layer 1b and an internal submicron electrode 7a formed in the digitated conducting layer 1a. The internal submicron electrodes 7a and 7b are addressed through opposite electrical edge connectors 5a and 5b. The internal submicron electrodes 7a and 7b face each other in the same plane within the well 8 and span less than the entire circumference of the well 8.

FIG. 5(*b*) illustrates a seventh embodiment of the laminated internal submicron electrode assembly of the present invention with interdigitated conducting layers. This embodiment is similar to the sixth embodiment shown in FIG. 5a but the wells 8 are arranged in a staggered, closely packed array which is more area efficient and in which they touch adjacent fingers of the digitated conducting layers 1a and 1b.

EXAMPLE 6

Figure 6:
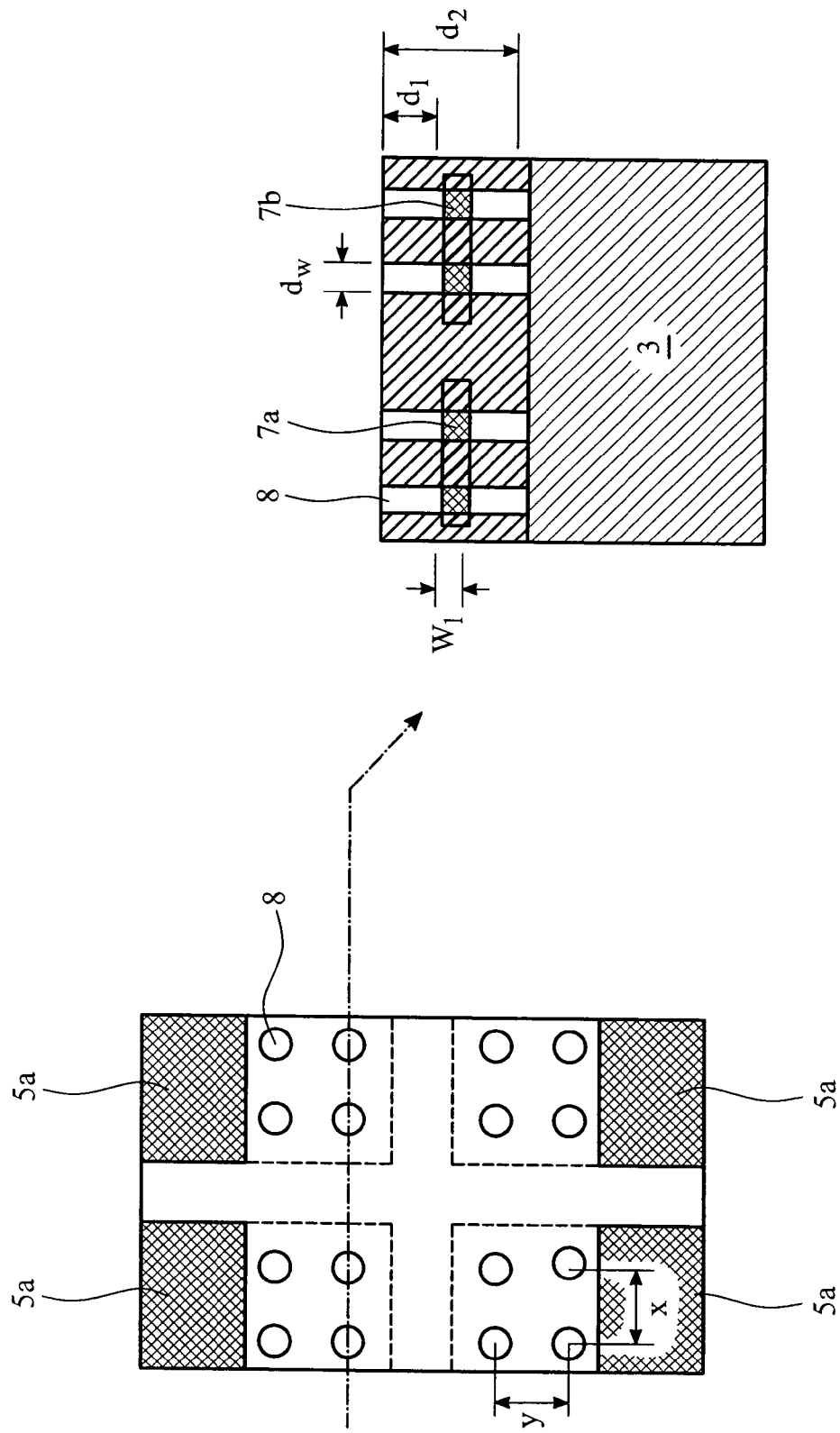
FIG. 6 illustrates in side view and plan view an eighth embodiment of the present invention with multiple internal submicron electrodes with independently addressable contact lips.

FIG. 6 illustrates an eighth embodiment of the electrode assembly of the present invention with four laterally spaced apart internal submicron electrodes (7a and 7b shown only in FIG. 6) co-planarly arranged on a single substrate 3. Each of the internal submicron electrodes 7a, 7b is independently addressable through edge electrical connectors 5a, 5b (with 5c and 5d for unseen internal submicron electrodes 7c and 7d respectively).

This embodiment constitutes multiple devices on a single substrate or multiple individually addressable electrode arrays on a single device (eg an array of several electrode arrays).

EXAMPLE 7

When either the conduction runs are long and thin or the conducting layers are extremely thin, problems relating to the resistivity between the internal submicron electrode and the edge contact may arise. The precise conditions under which this might occur will depend upon the dimensions of the electrode, the conduction characteristics of the electrode materials and the mechanical strength of the materials used. Conduction runs with high resistivity may be kept to a minimum by the use of vias which provide an efficient conduction pathway from the face of the electrode to the 'back plane' electrode which completes the connection to the edge electrical connector. This approach alleviates both IR drop issues (ensuring a constant electrode voltage at all points along the length of the electrode in the example shown in FIG. 11). This approach can be used as necessary with any of the embodiments described above. Another approach would be to bury (for example damascene) conducting tracks/planes with dimensions that are smaller than the internal submicron electrodes. The conducting layer is then deposited directly on top to provide a low resistivity interconnect to all the internal submicron electrodes. Another approach would be to construct a similar conducting pattern directly on top of the conducting layer.

EXAMPLE 8

Diffusion limited characteristics are observed clearly in cyclic voltammetry using a conventional platinum disc macroelectrode (area 0.378 $cm^2$) in aqueous KCl (0.1 M) with a background electrolyte containing potassium ferricyanide (10 mM) at a scan rate of 5 mV/s (see FIG. 12). The maximum and minimum are typical characteristics of diffusion limitation. Inefficient electrode processes are evidenced by hysteresis at either extreme of the potential sweep and the large separation of the forward and reverse sweeps are characteristic of unfavourable charging phenomena.

A defining aspect of a micro or nano scale electrode according to an embodiment of the invention is the absence of diffusion limitation which is evidenced by sigmoidal rather than peaked cyclic voltammograms. A cyclic voltammogram of a 0.05 micron thick electrode (50 μm width and 50 μm spacing) in ferricyanide (10 mM) with KCl (0.1 M) background electrolyte between 0.35 V and 0.00 V at 5 $mVs^{-1}$ is shown in FIG. 13. It can be seen that there is no evidence of diffusion limitation (no maximum or minimum). The scan rate is sufficiently low to demonstrate any overlap between neighbouring elements in the array (and thus a return to linear diffusion). In other words nanoelectrode behaviour is preserved even at slow scan rates. It should be emphasized that the overall current passed by the array is greater than 30 μA which is comparable with a macroelectrode (see FIG. 12) enabling the use of standard electrochemical measurement and control apparatus but with nanoelectrode characteristics and a total electrode area of $2.0 \times 10^{-5}$ $cm^2$ which is around 10000× times lower than the macroelectrode. This offers substantial signal to noise advantages. There is little evidence of hysteresis at the extremes of the potential sweep suggesting efficient electrode processes are occurring. The forward and reverse sweeps are not widely separated suggesting much reduced charging contributions.

EXAMPLE 9

A platinum cleaning cycle demonstrated that a preferred embodiment of the invention is a genuine platinum electrode displaying typical hydrogen and oxygen adsorption peaks (see FIG. 14).

A cyclic voltammogram for a platinum 0.05 micron thick electrode (20 μm hole dimension and 20 μm hole separation) was obtained in aqueous KCl (0.1 M) at a sweep rate of 100 $mVs^{-1}$ between 1.8 and −0.8 V with the overall current limited to 10 μA. Diagnostic peaks for hydrogen gas production and oxidation on platinum (near −0.5V) and a nucleation loop and associated peaks for oxide formation and reduction on platinum can clearly be seen near +1.2V (in particular on scan 5). There was an increase in the overall currents observed on cycling attributable to electrode cleaning and an expected increase in electrode geometric area on cycling.

The invention claimed is:

1. An electrode assembly having a laminate structure comprising:
   a first insulating capping layer;
   a first conducting layer capped by the first insulating capping layer and substantially encapsulated by at least the first insulating capping layer such that only an electrical contact lip of the first conducting layer is exposed; and
   an array of etched voids extending through at least the first insulating capping layer and the first conducting layer, wherein each void is partly bound by a surface of the first conducting layer which acts as an internal submicron electrode,
   wherein a thickness of the conducting layer is in the range of an atomic thickness to 0.99 microns, a depth of the internal submicron electrode is in the range of 0.05 to 10 microns, an etch depth of each void is in the range of 0.05 to 100 microns, a lateral dimension of each void is in the range of 10 to 100 microns and the array has a pitch in the range of 10 to 200 microns.

2. An electrode assembly as claimed in claim 1 comprising: a plurality of conducting layers (which may be the same or different) including the first conducting layer and a plurality of insulating capping layers including the first insulating capping layer, wherein the plurality of conducting layers and the plurality of insulating capping layers are alternating in the laminate structure, wherein each conducting layer is encapsulated to leave exposed only an electrical contact lip and the array of etched voids extends through the plurality of insulating capping layers and the plurality of conducting layers, wherein each void is partly bound by a surface of each of the plurality of conducting layers which acts as an internal submicron electrode.

3. An electrode assembly as claimed in claim 1 further comprising: a second conducting layer, wherein the first conducting layer is encapsulated to leave exposed only a first electrical contact lip and the second conducting layer is encapsulated to leave exposed only a second electrical contact lip, wherein the array of etched voids extends through the first conducting layer, the first insulating capping layer and the second conducting layer, wherein each void is partly bound by a surface of the first conducting layer which acts as an internal submicron electrode and/or by a surface of the second conducting layer which acts as an internal submicron electrode.

4. An electrode assembly as claimed in claim 1 comprising: a second conducting layer and a second insulating capping layer, wherein the first conducting layer is encapsulated to leave exposed only a first electrical contact lip and the second conducting layer is encapsulated to leave exposed only a second electrical contact lip, wherein the array of etched voids extends through the first conducting layer, the first insulating capping layer, the second conducting layer and the second insulating capping layer, wherein each void is partly bound by a surface of the first conducting layer which acts as an internal submicron electrode and/or by a surface of the second conducting layer which acts as an internal submicron electrode.

5. An electrode assembly as claimed in claim 3 wherein the first conducting layer and second conducting layer are substantially coplanar.

6. An electrode assembly as claimed in claim 3 wherein the first conducting layer and second conducting layer are axially spaced apart.

7. An electrode assembly as claimed in claim 1, wherein the array is in a linear or staggered pattern.

8. An electrode assembly as claimed in claim 1 wherein the first conducting layer is substantially encapsulated by only the first insulating capping layer such that only an electrical contact lip of the first conducting layer is exposed, wherein the array of etched voids extends through only the first insulating capping layer and the first conducting layer.

9. An electrode assembly as claimed in claim 1 further comprising:
   an insulating substrate layer,
   wherein the first conducting layer is fabricated on the insulating substrate layer and is substantially encapsulated by the first insulating capping layer and the insulating substrate layer such that only an electrical contact lip of the first conducting layer is exposed.

10. An electrode assembly as claimed in claim 1 further comprising:
    an insulating substrate layer;
    a second insulating capping layer fabricated on the insulating substrate layer, wherein the first conducting layer is fabricated on the second insulating capping layer and is substantially encapsulated by the first insulating capping layer and the second insulating capping layer such that only an electrical contact lip of the first conducting layer is exposed.

11. An electrode assembly as claimed in claim 1 further comprising:
    an insulating substrate layer;
    a second insulating capping layer,
    wherein the first conducting layer is fabricated on the second insulating capping layer and is substantially encapsulated by the first insulating capping layer and the second insulating capping layer such that only an electrical contact lip of the first conducting layer is exposed;
    a second conducting layer,
    wherein the second conducting layer is fabricated on the insulating substrate layer and is substantially encapsulated by the second insulating capping layer and the insulating substrate layer such that only an electrical contact lip of the second conducting layer is exposed,
    wherein the array of etched voids extends through at least the first insulating capping layer, the first conducting layer and the second insulating capping layer, wherein each void is partly bound by a surface of the first conducting layer which acts as an internal submicron electrode.

12. An electrode assembly as claimed in claim 1 wherein the array of etched voids extends through only the first insulating capping layer, the first conducting layer and the second insulating capping layer.

13. An electrode assembly as claimed in claim 1 wherein the array of etched voids extends through the first insulating capping layer, the first conducting layer, the second insulating capping layer and the second conducting layer, wherein each void is partly bound by a surface of the first conducting layer which acts as a first internal submicron electrode and by a surface of the second conducting layer which acts as a second internal submicron electrode.

14. An electrode assembly as claimed in claim 1 further comprising:

an insulating substrate layer;

a second conducting layer, wherein the first conducting layer is digitated and the second conducting layer is digitated, wherein the first conducting layer and the second conducting layer are interdigitally fabricated on the insulating substrate layer and are substantially encapsulated by the first insulating capping layer and the insulating substrate layer such that only an electrical contact lip of the first conducting layer and an electrical contact lip of the second conducting layer is exposed, wherein the array of etched voids extends through the first insulating capping layer, the first conducting layer and the second conducting layer, wherein each void is partly bound by a surface of the first conducting layer which acts as a first internal submicron electrode and is partly bound by a surface of the second conducting layer which acts as a second internal submicron electrode.

15. An electrode assembly as claimed in claim 1 further comprising:

an insulating substrate layer;

a second conducting layer, wherein the second conducting layer is substantially coplanar with the first conducting layer, wherein each of the first conducting layer and the second conducting layer is capped by the first insulating capping layer and is substantially encapsulated by at least the first insulating capping layer such that only an electrical contact lip of the first conducting layer and an electrical contact lip of the second conducting layer respectively is exposed, wherein one or more first etched voids extend through the first insulating capping layer and the first conducting layer and one or more second etched voids extend through the first insulating capping layer and the second conducting layer, wherein each first etched void is partly bound by a surface of the first conducting layer which acts as an internal submicron electrode and each second etched void is partly bound by a surface of the second conducting layer which acts as an internal submicron electrode.

16. An electrode assembly as claimed in claim 15 wherein each of the first conducting layer and the second conducting layer is substantially encapsulated by only the first insulating capping layer such that only an electrical contact lip of the first conducting layer and an electrical contact lip of the second conducting layer, respectively, is exposed.

17. An electrode assembly as claimed in claim 1, wherein the thickness of the (or each) conducting layer (which may be the same or different) is in the range 0.05 to 0.90 microns.

18. An electrode assembly as claimed in claim 1, wherein the depth of the (or the first) internal submicron electrode is 0.10 to 1 micron.

19. An electrode assembly as claimed in claim 1, wherein the etch depth of each void (which may be the same or different) is in the range of 0.10 to 10 microns.

20. An electrode assembly as claimed in claim 1 wherein the thickness of the (or each) conducting layer (which may be the same or different) is in the range 0.05 to 0.75 microns.

21. An electrode assembly as claimed in claim 1 wherein the thickness of the (or each) conducting layer (which may be the same or different) is in the range 0.05 to 0.49 microns.

22. An electrode assembly as claimed in claim 1 wherein the thickness of the (or each) conducting layer (which may be the same or different) is in the range 0.10 to 0.45 microns.

23. An electrode assembly as claimed in claim 1 wherein the depth of (or the first) internal submicron electrode is in the range of 0.15 to 0.5 microns.

* * * * *

UNITED STATES PATENT AND TRADEMARK OFFICE
CERTIFICATE OF CORRECTION

Page 1 of 1

PATENT NO.         : 9,097,654 B2
APPLICATION NO.    : 13/130878
DATED              : August 4, 2015
INVENTOR(S)        : Neville John Freeman et al.

It is certified that error appears in the above-identified patent and that said Letters Patent is hereby corrected as shown below:

On the title page, item (75), Line 1,

Delete "Tarporley" and insert
--Tarporley, Cheshire--, therefore

On the title page, item (75), Line 4,

Delete "Edingburgh" and insert
--Edinburgh--, therefore

In the specification,

Column 9, Line 42,

Delete "which" and insert
--which:--, therefore

Column 12, Line 5,

Delete "configuration," and insert
--configuration.--, therefore

Signed and Sealed this
Nineteenth Day of January, 2016

Michelle K. Lee
*Director of the United States Patent and Trademark Office*